(12) United States Patent
Yamaguchi et al.

(10) Patent No.: US 11,518,731 B2
(45) Date of Patent: Dec. 6, 2022

(54) FLUORINE-CONTAINING COMPOUND, SUBSTRATE FOR PATTERNING, PHOTODEGRADABLE COUPLING AGENT, PATTERNING METHOD, AND COMPOUND

(71) Applicants: Kanagawa University, Yokohama (JP); NIKON CORPORATION, Tokyo (JP)

(72) Inventors: Kazuo Yamaguchi, Yokohama (JP); Yusuke Kawakami, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 388 days.

(21) Appl. No.: 16/193,526

(22) Filed: Nov. 16, 2018

(65) Prior Publication Data

US 2019/0085004 A1 Mar. 21, 2019

Related U.S. Application Data

(60) Division of application No. 15/013,193, filed on Feb. 2, 2016, now abandoned, which is a continuation of application No. PCT/JP2014/072257, filed on Aug. 26, 2014.

(30) Foreign Application Priority Data

Aug. 27, 2013 (JP) .................................. 2013-176023

(51) Int. Cl.
| | | |
|---|---|---|
| *C07C 205/12* | (2006.01) | |
| *C07C 205/36* | (2006.01) | |
| *C07C 205/37* | (2006.01) | |
| *G03F 7/20* | (2006.01) | |
| *C07F 7/18* | (2006.01) | |
| *C07D 207/46* | (2006.01) | |
| *G03F 7/075* | (2006.01) | |
| *G03F 7/16* | (2006.01) | |

(52) U.S. Cl.
CPC .......... *C07C 205/37* (2013.01); *C07C 205/12* (2013.01); *C07C 205/36* (2013.01); *C07D 207/46* (2013.01); *C07F 7/1804* (2013.01); *G03F 7/0755* (2013.01); *G03F 7/16* (2013.01); *G03F 7/20* (2013.01)

(58) Field of Classification Search
CPC .... G03F 7/2002; G03F 7/2004; C07F 7/1804; C07D 207/46; C07C 205/12; C07C 205/36; C07C 205/37
See application file for complete search history.

(56) References Cited

U.S. PATENT DOCUMENTS

| | | |
|---|---|---|
| 7,112,397 B2 | 9/2006 | Ozaki |
| 7,393,515 B2 | 7/2008 | Hoshino |
| 7,479,362 B2 | 1/2009 | Fukushima |
| 7,829,501 B2 | 11/2010 | Nakamura et al. |
| 9,606,437 B2 | 3/2017 | Yamaguchi |
| 2006/0222865 A1 | 10/2006 | Hoshino et al. |
| 2008/0318779 A1 | 12/2008 | Nakamura et al. |
| 2015/0168836 A1 | 6/2015 | Yamaguchi |
| 2016/0152642 A1 | 6/2016 | Yamaguchi et al. |

FOREIGN PATENT DOCUMENTS

| | | |
|---|---|---|
| EP | 1 736 477 A1 | 12/2006 |
| JP | 2003-321479 | 11/2003 |
| JP | 2006-276643 | 10/2006 |
| JP | 2007-23007 | 2/2007 |
| JP | 2008-50321 | 3/2008 |
| JP | 2008-171978 A1 | 7/2008 |
| WO | WO 2005/054256 A1 | 6/2005 |
| WO | WO 2006/016708 A1 | 2/2006 |
| WO | WO 2014/038579 A1 | 3/2014 |

OTHER PUBLICATIONS

Japanese Office Action for Japanese Application No. 2015-534222 dated Oct. 10, 2017.
Office Action dated Sep. 7, 2017 in U.S. Appl. No. 15/433,314.
Japanese Office Acton for Japanese Application No. 2014-534383 dated Apr. 25, 2017.
PCT International Search Report dated Dec. 10, 2013 in International Patent Application No. PCT/JP2013/073771.
PCT Written Opinion of the International Searching Authority dated Dec. 10, 2013 in International Patent Application No. PCT/JP2013/073771.
Zheng et al., "Design, Synthesis, and Structure-Activity Relationship, Molecular Modeling, and NMR Studies of a Series of Phenyl Alkyl Ketones as Highly Potent and Selective Phosphodiesterase-4 Inhibitors", Journal of Medicinal Chemistry, vol. 51, 2008, pp. 7673-7688.
Chinese Office Action dated Jan. 26, 2016 in Chinese Patent Application No. 201380045709.7.
U.S. Notice of Allowance dated Nov. 28, 2016 in U.S. Appl. No. 14/635,583.
U.S. Ex Parte Quayle Action dated Sep. 26, 2016 in U.S. Appl. No. 14/635,583.

(Continued)

Primary Examiner — John S Chu

(57) ABSTRACT

A method for producing a fluorine-containing compound represented by General formula (1), wherein X represents a halogen atom or an alkoxy group, $R^1$ represents a hydrogen atom or a linear, branched, or cyclic alkyl group having 1 to 10 carbon atoms, $R^{f1}$ and $R^{f2}$ are each independently a fluorinated alkoxy group, and n represents an integer of 0 or more.

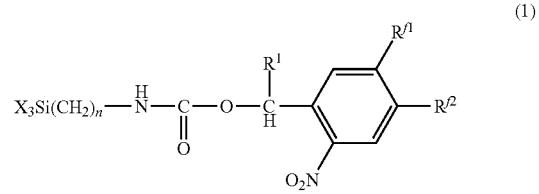

(1)

3 Claims, 2 Drawing Sheets

(56) References Cited

OTHER PUBLICATIONS

U.S. Office Action dated Jun. 9, 2016 in U.S. Appl. No. 14/635,583.
U.S. Restriction Requirement dated Mar. 25, 2016 in U.S. Appl. No. 14/635,583.
Konishi et al., "Evaluation of self-assembled monolayer formed by 2-notrpbenzyl etsertype photodegradable silane coupling agent substituted with double-chain fluorinated alkoxy group", $61^{st}$ SPSJ Symposium on Macromolecules, Polymer Preprints, Japan, vol. 61, No. 2, Sep. 5, 2012, 6 pages, 1Pa103.
Hashimoto et al., "Evaluation of surface modified with photodegradable ester type silane coupling agent having double-chain fluorinated alkoxy or alkoxy group", $57^{TH}$ SPSJ Annual Meeting, Polymer Preprints, Japan, vol. 57, No. 1, May 8, 2008, 6 pages, 3Pa155.
Konishi et al., "Preparation and Evaluation of 2-nitrobenzyl carbamate type photoresponsive self-assembled monolayer for organic film transistors", $62^{nd}$ SPSJ Symposium on Macromolecules, Japan, vol. 62, No. 2, 2013, 5 pages, 1PD072.
International Search Report dated Nov. 18, 2014 in corresponding International Patent Application No. PCT/JP2014/072257.
Written Opinion of the International Searching Authority dated Nov. 18, 2014 in corresponding International Patent Application No. PCT/JP2014/072257.
Office Action dated Aug. 24, 2018 in U.S. Appl. No. 15/013,193.
Office Action dated May 7, 2018 in U.S. Appl. No. 15/013,193.
Notification of Reopening of Prosecution Due to Consideration of an Information Disclosure Statement Filed After Mailing of a Notice of Allowance dated Feb. 2, 2018 in U.S. Appl. No. 15/013,193.
Notice of Allowance dated Nov. 3, 2017 in U.S. Appl. No. 15/013,193.
Office Action dated Apr. 6, 2017 in U.S. Appl. No. 15/013,193.
Office Action dated Dec. 15, 2016 in U.S. Appl. No. 15/013,193.
U.S. Appl. No. 15/433,314, filed Feb. 15, 2017, Kazuo Yamaguchi, Kanagawa University; Nikon Corporation.
U.S. Appl. No. 14/635,583 (U.S. Pat. No. 9,606,437), filed Mar. 2, 2015 (issued Mar. 28, 2017), Kazuo Yamaguchi, Kanagawa University; Nikon Corporation.
U.S. Appl. No. 15/013,193, filed Feb. 2, 2016, Kazuo Yamaguchi, Kanagawa University; Nikon Corporation.

FLUORINE-CONTAINING COMPOUND, SUBSTRATE FOR PATTERNING, PHOTODEGRADABLE COUPLING AGENT, PATTERNING METHOD, AND COMPOUND

CROSS-REFERENCE TO RELATED APPLICATIONS

This application is a divisional of U.S. Ser. No. 15/013,193, filed Feb. 2, 2016, which is a continuation of International Application PCT/JP2014/072257, filed on Aug. 26, 2014 and claims priority to Japanese Patent Application No. 2013-176023, filed on Aug. 27, 2013, the contents of which are incorporated herein by reference.

FIELD

The present invention relates to a fluorine-containing compound, a substrate for patterning, a photodegradable coupling agent, a patterning method, and a compound.

In recent years, in the production of micro-devices such as a semiconductor element, an integrated circuit, and a device for an organic EL display, a method in which patterns having different surface characteristics are formed on a substrate and a micro-device is manufactured by using the difference in the surface characteristics has been proposed.

As a patterning method using the difference in the surface characteristics on a substrate, there is a method in which a hydrophilic region and a water-repellent region are formed on a substrate, and an aqueous solution of a functional material is applied to the hydrophilic region. In this method, since the aqueous solution of the functional material is wet and spread only in the hydrophilic region, a thin film pattern of the functional material can be formed.

Recently, as the material capable of forming a hydrophilic region and a water-repellent region on a substrate, a coupling agent has been used in recent years. In Japanese Unexamined Patent Application, First Publication No. 2008-50321, a photodegradable coupling agent is described, wherein the photodegradable coupling agent can change the contact angle significantly before and after light irradiation, that is, which can change the hydrophilic characteristics and the water-repellent characteristics significantly before and after light irradiation.

SUMMARY

However, in the photodegradable coupling agent as described in Japanese Unexamined Patent Application, First Publication No. 2008-50321, there is still room for improvement in a difference in the contact angles before and after light irradiation and in sensitivity to the irradiated light.

The present invention has been made by taking into consideration the above situations and has an object to provide a fluorine-containing compound useful as a coupling agent, which has a large difference in contact angles between before and after light irradiation and has superior sensitivity; a substrate for patterning using the fluorine-containing compound; a photodegradable coupling agent using the fluorine-containing compound; a patterning method; and a compound useful as an intermediate in the production of the fluorine-containing compound.

A first aspect of the present invention is a fluorine-containing compound represented by the following General formula (1).

[Chem. 1]

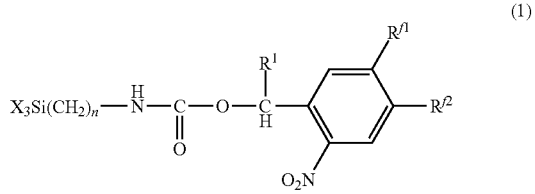

In General formula (1), X represents a halogen atom or an alkoxy group, $R^1$ represents a hydrogen atom or a linear, branched, or cyclic alkyl group having 1 to 10 carbon atoms, $R^{f1}$ and $R^{f2}$ are each independently a fluorinated alkoxy group, and n represents an integer of 0 or more.

A second aspect of the present invention is a substrate for patterning, which has a surface chemically modified with the fluorine-containing compound according to the first aspect.

A third aspect of the present invention is a photodegradable coupling agent consisted of the fluorine-containing compound according to the first aspect.

A fourth aspect of the present invention is a patterning method for forming a pattern on a surface to be treated of an object, which comprises a first step of chemically modifying the surface to be treated using the fluorine-containing compound according to the first aspect, a second step of producing a latent image formed of a hydrophilic region and a water-repellent region by irradiating the chemically modified surface to be treated with light having a predetermined pattern, and a third step of disposing a patterning material on the hydrophilic region or the water-repellent region.

A fifth aspect of the present invention is a patterning method for forming a circuit pattern for an electronic device on a flexible substrate, which comprises a first step of chemically modifying the entire surface or a specific region of the substrate using the fluorine-containing compound according to the first aspect, a second step of producing a latent image of the circuit pattern on the surface of the substrate by using the difference in the hydrophilicity and the water repellency by irradiating the surface of the chemically modified substrate with light energy having a distribution corresponding to the circuit pattern, and a third step of bringing the flexible patterning material into contact with the latent image portion on the surface of the substrate, and thereby capturing the patterning material in the shape of the circuit pattern by using the difference in the hydrophilicity and the water repellency.

In the patterning method of the fourth or fifth aspect of the present invention, the patterning material preferably includes a liquid conductive material, a liquid semiconductor material, or a liquid insulating material, and the light preferably includes light at a wavelength in the range of 200 nm to 450 nm.

A sixth aspect of the present invention is a compound represented by the following General formula (f).

[Chem. 2]

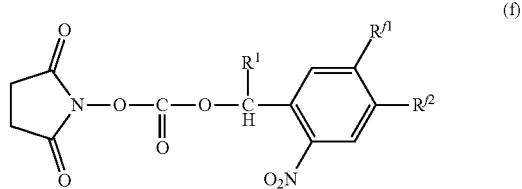

(f)

In General formula (f), $R^1$ represents a hydrogen atom or a linear, branched, or cyclic alkyl group having 1 to 10 carbon atoms, and $R^{f1}$ and $R^{f2}$ are each independently a fluorinated alkoxy group.

According to the present invention, it is possible to provide a fluorine-containing compound useful as a coupling agent, which has a large difference in contact angles between before and after light irradiation and has superior sensitivity; a substrate for patterning using the fluorine-containing compound; a photodegradable coupling agent using the fluorine-containing compound; a patterning method; and a compound useful as an intermediate in the production of the fluorine-containing compound.

DESCRIPTION OF EMBODIMENTS

<<Fluorine-Containing Compound>>

Figure 1:
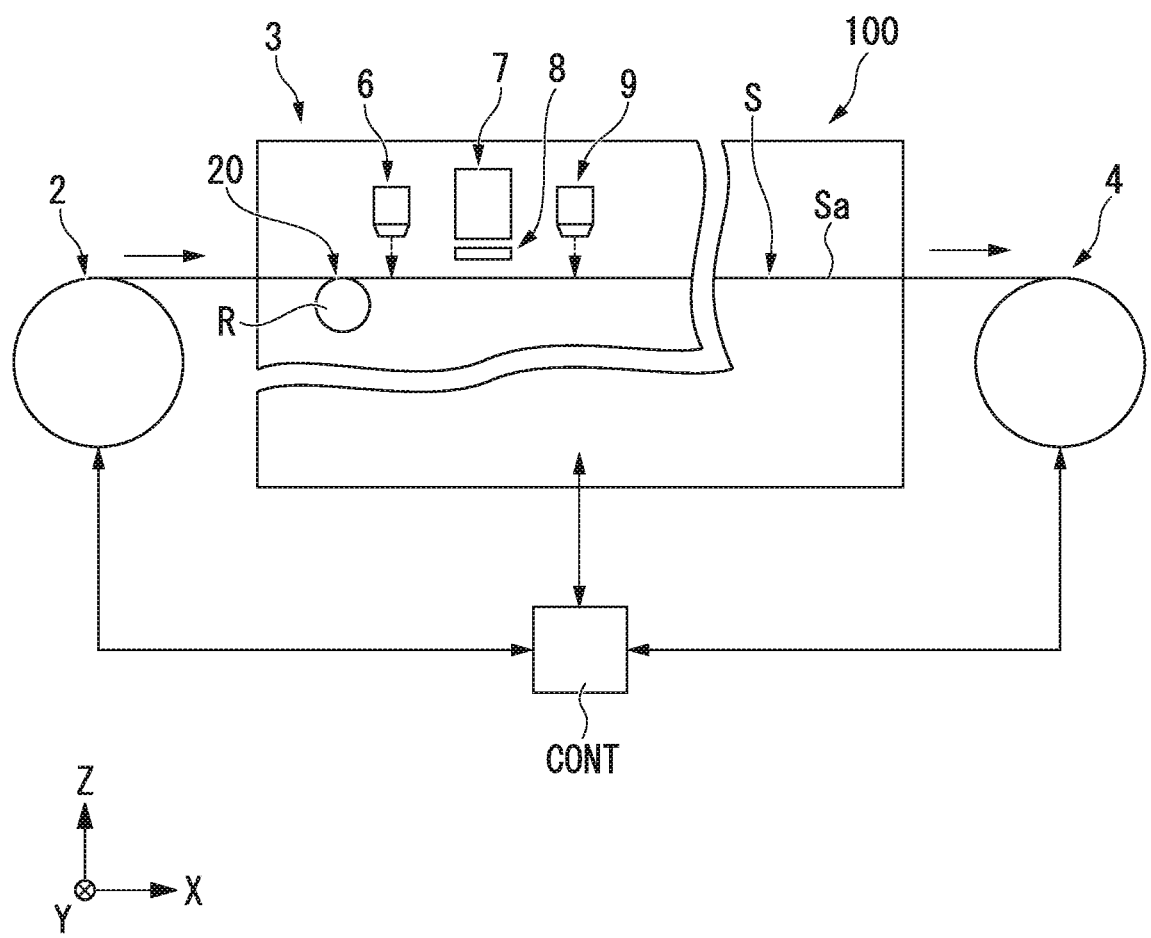
FIG. 1 is a schematic view showing the entire configuration of a suitable substrate-treating apparatus in the patterning method of the present invention.

The first aspect of the present invention is a fluorine-containing compound represented by the following General formula (1).

[Chem. 3]

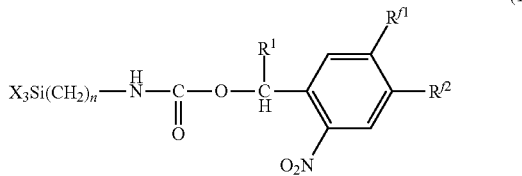

(1)

wherein X represents a halogen atom or an alkoxy group, $R^1$ represents a hydrogen atom or a linear, branched, or cyclic alkyl group having 1 to 10 carbon atoms, $R^{f1}$ and $R^{f2}$ are each independently a fluorinated alkoxy group, and n represents an integer of 0 or more.

In General formula (1), X is a halogen atom or an alkoxy group.

Examples of the halogen atom of X include a fluorine atom, a chlorine atom, a bromine atom, and an iodine atom.

The alkoxy group of X preferably has 1 to 20 carbon atoms, more preferably 1 to 10 carbon atoms, still more preferably 1 to 5 carbon atoms, desirably 1 to 3 carbon atoms, and most desirably 1 or 2 carbon atoms.

X is preferably an alkoxy group rather than a halogen atom.

n represents an integer of 0 or more. In terms of easy availability of starting raw materials, n is preferably an integer of 1 to 20, and more preferably an integer of 2 to 15. Further, n is preferably 3 or more, and more preferably 4 or more.

In General formula (1), $R^1$ is a hydrogen atom, or a linear, branched, or cyclic alkyl group having 1 to 10 carbon atoms.

As the alkyl group of $R^1$, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group, and a neopentyl group.

Examples of the cyclic alkyl group include a group in which 1 or more hydrogen atoms are removed from a monocycloalkane; or a polycycloalkane such as bicycloalkane, tricycloalkane, and tetracycloalkane.

In the present invention, $R^1$ is preferably a hydrogen atom, a methyl group, an ethyl group, an n-propyl group, or an isopropyl group.

In General formula (1), $R^{f1}$ and $R^{f2}$ are each independently a fluorinated alkoxy group.

In General formula (1), the fluorinated alkoxy group of $R^{f1}$ or $R^{f2}$ is preferably an alkoxy group having 3 or more carbon atoms, and may be partially fluorinated or may be a perfluoroalkoxy group. In the present invention, the fluorinated alkoxy group is preferably a fluorinated alkoxy group which is partially fluorinated.

In the present invention, examples of the fluorinated alkoxy group of $R^{f1}$ or $R^{f2}$ include groups represented by $—O—(CH_2)_{n^{f1}}—(C_{n^{f2}}F_{2n^{f2}+1})$. $n^{f1}$ is an integer of 0 or more and $n^{f2}$ is an integer of 1 or more.

In the present invention, $n^{f1}$ is preferably 0 to 30, more preferably 0 to 15, and most preferably 0 to 5.

Furthermore, in the present invention, $n^{f2}$ is preferably 1 to 30, more preferably 1 to 15, still more preferably 1 to 10, and most preferably 1 to 6.

Specific examples of the fluorine-containing compound represented by General formula (1) are shown below.

[Chem. 4]

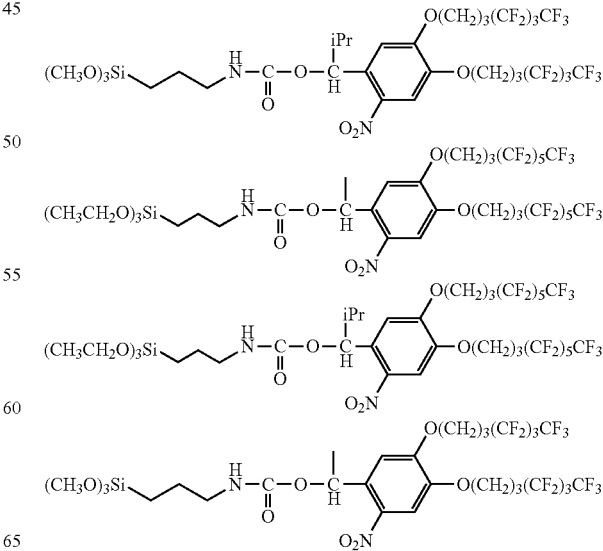

<<Compound>>

The sixth aspect of the present invention is a compound represented by the following General formula (f).

[Chem. 5]

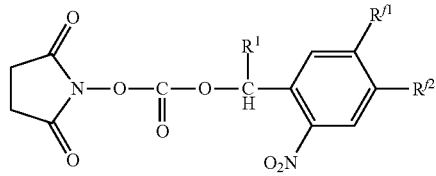
(f)

wherein R¹ represents a hydrogen atom or a linear, branched, or cyclic alkyl group having 1 to 10 carbon atoms, and $R^{f1}$ and $R^{f2}$ are each independently a fluorinated alkoxy group.]

In General formula (f), the descriptions of $R^1$, $R^{f1}$, and $R^{f2}$ are each the same as those of $R^1$, $R^{f1}$ and $R^{f2}$ in aforementioned General formula (1).

<Method for Producing Fluorine-Containing Compound>

The fluorine-containing compound of the present invention is preferably produced using the compound according to the sixth aspect of the present invention as a raw material (intermediate).

Examples of the solvent used in the following steps include such as ethyl acetate, butyl acetate, acetone, methyl ethyl ketone, methyl isobutyl ketone, cyclohexanone, tetrahydrofuran, dioxane, N,N-dimethylformamide, N,N-dimethylacetamide, benzene, toluene, acetonitrile, methylene chloride, chloroform, dichloroethane, methanol, ethanol, 1-propanol, 2-propanol, and 1-butanol. These may be used alone or in combination of two or more kinds thereof.

The compound according to the sixth aspect of the present invention can be obtained, for example, through the following respective steps.

[Chem. 6]

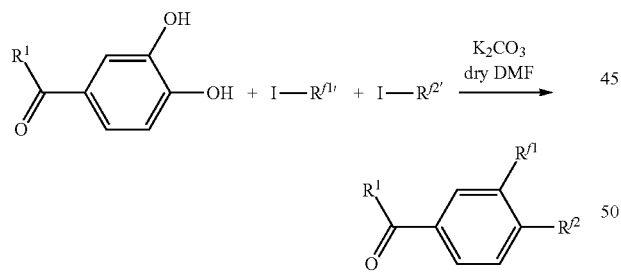

In the above formulae $R^1$, $R^{f1}$, and $R^{f2}$ are the same as $R^1$, $R^{f1}$, and $R^{f2}$ in aforementioned General formula (1). $R^{f1'}$ and $R^{f2'}$ in I—$R^{f1'}$ and I—$R^{f2'}$ are the same as $R^{f1}$ and $R^{f2}$, respectively.

[Chem. 7]

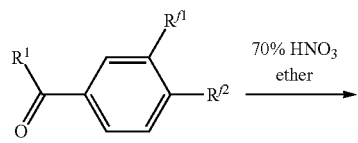

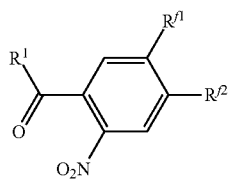

In the above formulae, $R^1$, $R^{f1}$, and $R^{f2}$ are the same as $R^1$, $R^{f1}$, and $R^{f2}$ in aforementioned General formula (1), respectively.

[Chem. 8]

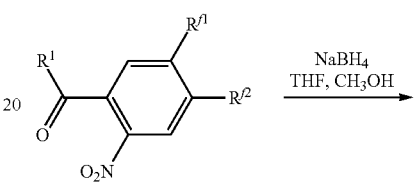

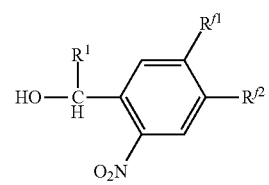

In the above formulae, $R^1$, $R^{f1}$, and $R^{f2}$ are each the same as $R^1$, $R^{f1}$, and $R^{f2}$ in General formula (1).

[Chem. 9]

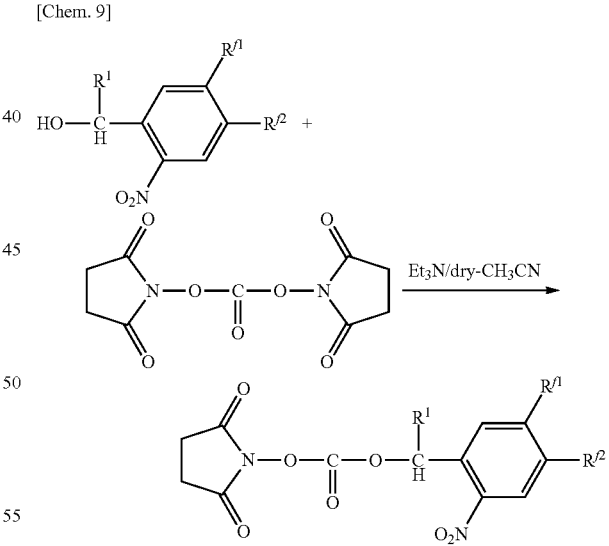

In the above reaction scheme, the explanations of $R^1$, $R^{f1}$, and $R^{f2}$ are the same as those of $R^1$, $R^{f1}$, and $R^2$ in aforementioned General formula (1), respectively.

The fluorine-containing compound according to the first aspect of the present invention can be obtained by the following steps, for example. In the following formulae, the explanations of X, $R^1$, $R^{f1}$, $R^{f2}$, and n are the same as those of X, $R^1$, $R^{f1}$, $R^{f2}$, and n in aforementioned General formula (1), respectively.

[Chem. 10]

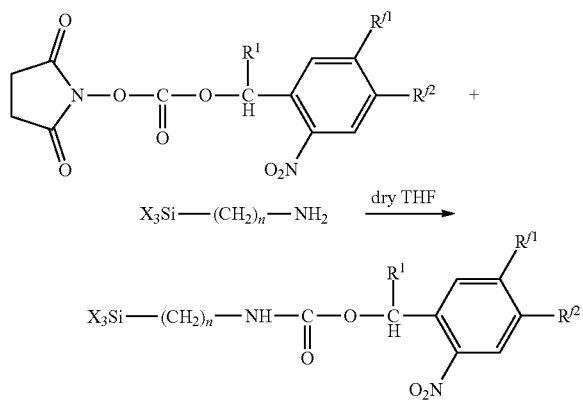

<Surface Modification in 2-Steps>

A case of performing a surface modification in 2-steps using the fluorine-containing compound of the present invention will be described. First, a substrate surface is subjected to surface modification of the substrate using the fluorine-containing compound of the present invention, as shown in [First Step], thereby making the substrate surface water-repellent. Thereafter, the contact angle of the substrate surface is reduced by carrying out light irradiation, thereby making the substrate surface of the water-repellent substrate hydrophilic.

Furthermore, a terminal carbonate compound or the like is reacted with the substrate which has been made hydrophilic in the first step, as shown in the following second step, thereby significantly increasing the contact angle of the substrate surface which has been made hydrophilic in the first step, and thus, making the surface water-repellent.

In the following formulae, $R^f$ is a fluorine atom-containing group for imparting water repellency on the substrate surface and examples thereof include the fluorinated alkoxy groups of aforementioned $R^{f1}$ and $R^{f2}$.

[Chem. 11]

[First step]

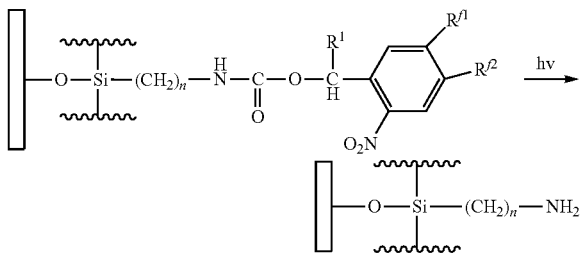

[Second step]

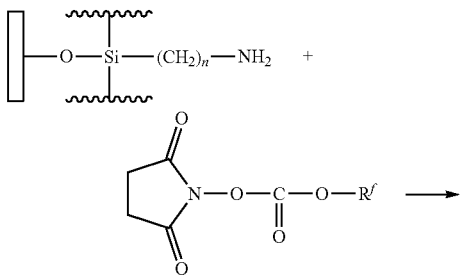

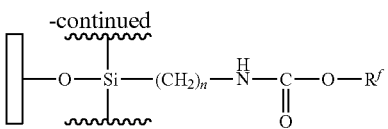

-continued

<<Substrate for Patterning>>

The second aspect of the present invention is a substrate for patterning, which has a surface chemically modified with the fluorine-containing compound.

The material for the substrate is not particularly limited and preferred examples thereof include glass, quartz glass, a silicon wafer, a plastic plate, and a metal plate. In addition, a substrate on which a metal thin film has been formed may be used.

The shape of the substrate is not particularly limited, but a planar surface, a curved surface, or a planar surface having partially a curved surface is preferable, and a planar surface is more preferable. Further, the surface area of the substrate is also not particularly limited, but a substrate having a large surface within a range in which applying methods in the related art can be used may be employed. In addition, the surface chemically modified with the fluorine-containing compound is preferably formed on one side of the planner substrate.

When modifying the surface of the substrate, it is preferable to subject the substrate surface a pretreatment. As the pretreatment method, a pretreatment in a piranha solution or a pretreatment by a UV-ozone cleaner is preferable.

The method for modifying the surface of the substrate is not particularly limited as long as it is a method in which at least a part of X bonded to reactive Si in General formula (1) is dissociated and thereby, the substrate is bonded to the fluorine-containing compound after the dissociation. Thus, known methods such as a dipping method and a chemical treatment method can be used.

<<Photodegradable Coupling Agent>>

The third aspect of the present invention is a photodegradable coupling agent consisted of the fluorine-containing compound.

The photodegradable coupling agent according to the present aspect has a photodegradable group having a liquid repellent group and an attaching group X linked to the photodegradable group through a functional group, in which the liquid repellent group has fluorinated alkoxy chains $R^{f1}$ and $R^{f2}$ at the terminal thereof and the functional group has an amino group as a residue after photodegradation. Therefore, in the photodegradable coupling agent of the present invention, a large difference in contact angles between before and after light irradiation can be secured.

<<Patterning Method>>

The fourth aspect of the present invention is a patterning method for forming a pattern on a surface to be treated of an object, which includes a first step of chemically modifying a surface to be treated using the fluorine-containing compound according to the first aspect; a second step of producing a latent image formed of a hydrophilic region and a water-repellent region by irradiating the surface to be treated which has been chemically treated with light having a predetermined pattern, and a third step of disposing a patterning material on the hydrophilic region or the water-repellent region.

[First Step]

In the patterning method for forming a pattern on a surface to be treated of an object, the first step is a step of chemically modifying the surface to be treated using the fluorine-containing compound according to the first aspect.

The object is not particularly limited. Examples thereof include a metal, a crystalline material (for example, a single crystalline material, a polycrystalline material, and a partially crystalline material), an amorphous material, a conductor, a semiconductor, an insulator, an optical element, a coated substrate, fiber, glass, ceramics, zeolite, plastic, a thermosetting and thermoplastic material (for example, doped in some cases: such as polyacrylate, polycarbonate, polyurethane, polystyrene, a cellulose polymer, polyolefin, polyamide, polyimide, a resin, polyester, and polyphenylene), a film, a thin film, and a foil.

The patterning method according to the present aspect is preferably a patterning method in which a circuit pattern for an electronic device is formed on a flexible substrate. That is, the object is preferably a flexible substrate.

Here, the term flexibility refers to a property capable of flexing the substrate without being broken or fractured even when a force of about its own weight is applied to the substrate. Further, properties of bending by force of about its own weight are also included in the flexibility. Moreover, the flexibility varies depending on such as the material, the size, the thickness of the substrate, and the environment such as a temperature. In addition, as the substrate, a single belt-shape substrate may be used, or the substrate may be configured to be formed in the belt shape by connecting a plurality of unit substrates.

As the flexible substrate (object), for example, a resin film or a foil of stainless steel or the like can be used. For example, as the resin film, materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin can be used.

In the first step, the entire surface to be treated of an object may be chemically modified by using the fluorine-containing compound; however it is preferable that a specific region of an object be chemically modified by using the fluorine-containing compound.

The method for modifying the surface to be treated of an object is not particularly limited as long as it is a method in which at least a part of X bonded to reactive Si in aforementioned General formula (1) is dissociated and thus, the substrate is bonded to the fluorine-containing compound after the dissociation. Therefore, known methods such as a dipping method and a chemical treatment method can be used.

An example of the chemical modification in the first step is shown below. In the following formulae, the explanations of X, $R^1$, $R^{f1}$, $R^{f2}$, and n are the same as those of X, $R^1$, $R^{f1}$, $R^{f2}$, and n in aforementioned General formula (1), respectively.

[Chem. 12]

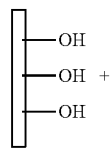

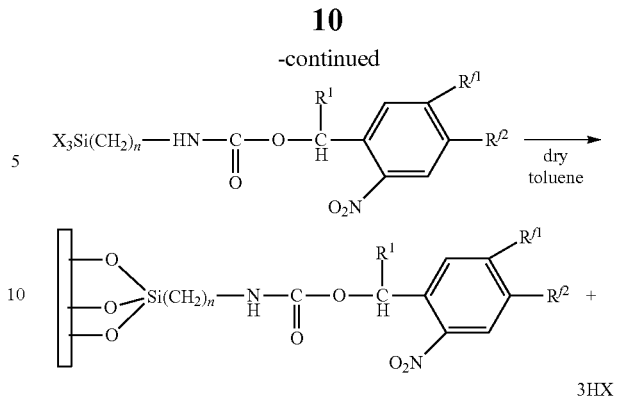

[Second Step]

The second step is a step of producing a latent image formed of a hydrophilic region and a water-repellent region by irradiating the chemically modified surface to be treated with light having a predetermined pattern.

As the light to be irradiated, ultraviolet rays are preferable. The light to be irradiated preferably includes light having a wavelength included in a range of 200 nm to 450 nm, more preferably includes light having a wavelength included in a range of 320 nm to 450 nm. In addition, it is also preferable that light including light having a wavelength of 365 nm be irradiated. Light having these wavelengths can efficiently degrade the photodegradable group according to the aspects of the present invention.

Examples of a light source include a low-pressure mercury lamp, a high-pressure mercury lamp, an ultrahigh-pressure mercury lamp, a xenon lamp, and a sodium lamp; a laser of a gas such as nitrogen, a liquid laser of an organic dye solution, and a solid laser in which rare earth ions are contained in inorganic single crystals. In addition, as a light source other than lasers, from which monochromatic light is obtained, light at a specific wavelength extracted with a broadband line spectrum or a continuous spectrum using an optical filter such as a band-pass filter and a cut-off filter may be used. The high-pressure mercury lamp or the ultrahigh-pressure mercury lamp is preferable as a light source from the viewpoint that a large area can be irradiated using the mercury lamp by one irradiation.

In the patterning method of the present invention, a surface to be treated can be irradiated with light arbitrarily within the above range. However, in particular, a surface to be treated is preferably irradiated with light energy having a distribution corresponding to a circuit pattern.

In the second step, a residue (amino group) having hydrophilicity is generated due to dissociation of a group having water-repellency by irradiating the chemically modified surface to be treated with light having a predetermined pattern. Therefore, after light irradiation, it is possible to form a latent image consisted of a hydrophilic region and a water-repellent region.

In the second step, it is possible to produce a latent image of a circuit pattern by using a difference in the hydrophilicity and the water repellency on the surface of a flexible substrate by irradiation with light corresponding to the circuit pattern.

An example of the steps in which a residue (amino group) having hydrophilicity generated by the irradiating the chemically modified surface to be treated with light having a predetermined pattern and the dissociation of a group having water-repellency is produced is shown below. In the following formulae, the descriptions of $R^1$, $R^{f1}$, $R^{f2}$, and n are the same as those of $R^1$, $R^{f1}$, $R^{f2}$, and n in aforementioned General formula (1), respectively.

[Chem. 13]

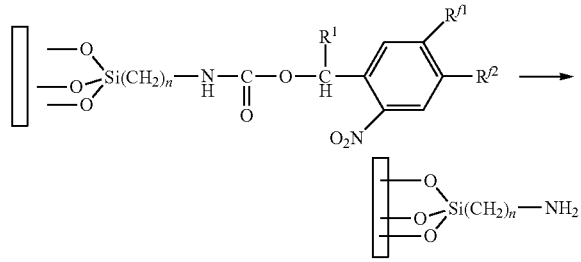

[Third Step]

The third step is a step of disposing a patterning material in the hydrophilic region or the water-repellent region, each of which has been produced in the second step.

Examples of the patterning material include wiring materials (metal solutions) in which particles of gold, silver, copper, an alloy of these, or the like are dispersed in a predetermined solvent, electronic materials in which a precursor solution including the above-described metals, an insulator (resin), a semiconductor, an organic EL light-emitting material, or the like is dispersed in a predetermined solvent, or resist solutions.

In the patterning method according to the present aspect, the patterning material is preferably a liquid conductive material, a liquid semiconductor material, or a liquid insulating material.

Examples of the liquid conductive material include a patterning material formed of a dispersion in which conductive fine particles are dispersed in a dispersion medium. As the conductive fine particles, for example, in addition to metal fine particles containing any one of gold particles, silver particles, copper particles, palladium particles, nickel particles, and ITO particles, fine particles of oxides thereof or of a conductive polymer or a superconductor are used.

These conductive fine particles can also be used after the surfaces thereof are coated with an organic material in order to improve dispersibility.

The dispersion medium is not particularly limited as long as it can disperse the above-described conductive fine particles and does not cause aggregation of the fine particles. In addition to water, examples of the dispersion medium include alcohols such as methanol, ethanol, propanol, and butanol; hydrocarbon-based compounds such as n-heptane, n-octane, decane, dodecane, tetradecane, toluene, xylene, cymene, durene, indene, dipentene, tetrahydronaphthalene, decahydronaphthalene, cyclohexyl benzene; ether-based compounds such as ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, 1,2-dimethoxyethane, bis(2-methoxyethyl)ether, and p-dioxane; and polar compounds such as propylene carbonate, y-butyrolactone, N-methyl-2-pyrrolidone, dimethyl formamide, dimethyl sulfoxide, and cyclohexanone. Among these, from the viewpoint of dispersibility of fine particles and stability of a dispersion and ease of application to a liquid droplet discharge method (ink jet method), water, alcohols, a hydrocarbon-based compound, and an ether-based compound are preferable, and more preferred examples of the dispersion medium include water and a hydrocarbon-based compound.

As the liquid semiconductor material, an organic semiconductor material dispersed or dissolved in a dispersion medium can be used. Examples of the organic semiconductor material include a n-electron conjugated system polymer material of which the skeleton is configured of conjugated double bonds is preferable. Representative examples of the organic semiconductor material include soluble polymeric materials such as polythiophene, poly(3-alkylthiophene), polythiophene derivatives, and pentacene.

Examples of the liquid insulating material include insulating materials in which polyimide, polyamide, polyester, acryl, phosphorus glass (PSG), boron phosphorus glass (BPSG), polysilazane-based SOG, silicate-based Spin on Glass (SOG), alkoxy silicate-based SOG $SiO_2$ having a Si—$CH_3$ bond represented by a siloxane polymer, or the like is dispersed or dissolved in a dispersion medium.

In the third step, as a method for disposing a patterning material on the hydrophilic region or the water-repellent region of the surface to be treated, a liquid droplet discharge method, an ink jet method, a spin coating method, a roll coating method, a slot coating method, or the like can be applied.

Hereinafter, the patterning method according to the aspect of the present invention will be described with reference to a drawing.

In the patterning method according to the present aspect, in the case where a flexible substrate able to be used in a so-called roll-to-roll process is used, a pattern may be formed by using a substrate-treating apparatus 100 which is a roll-to-roll apparatus, as shown in FIG. 1. FIG. 1 shows a configuration of the substrate-treating apparatus 100.

As shown in FIG. 1, the substrate-treating apparatus 100 has a substrate-supplying unit 2 that supplies a belt-shape substrate (for example, a belt-shape film member) S, a substrate-treating unit 3 that performs a treatment to the surface (surface to be treated) Sa of the substrate S, a substrate-retrieving unit 4 that retrieves the substrate S, an applying unit 6 of a fluorine-containing compound, an exposing unit 7, a mask 8, a patterning material material-applying unit 9, and a controlling unit CONT, that controls each of these parts. In the substrate-treating unit 3, various treatments can be performed on the surface of the substrate S between from the time when the substrate S is sent from the substrate-supplying unit 2 to the time when the substrate S is retrieved by the substrate-retrieving unit 4.

The substrate-treating apparatus 100 can be suitably used in the case where a display element (electronic device) such as an organic EL element and a liquid crystal display element is formed on the substrate S.

Moreover, FIG. 1 is an illustration of a method using a photomask to produce a desired pattern light. However, the present invention can also be suitably applied to a maskless exposure method in which a photomask is not used. Examples of the maskless exposure method in which a pattern light is produced without using a photomask include a method in which a spatial light modulation element such as a DMD is used and a method in which a spot light is scanned, such as a laser beam printer.

In the patterning method according to the present aspect, a XYZ coordinate system is set as shown in FIG. 1. Hereinafter, description is made using the XYZ coordinate system as appropriate. In the XYZ coordinate system, for example, an X-axis and a Y-axis are set along a horizontal plane, and a Z-axis is set upward along the vertical direction. In addition, the substrate-treating apparatus 100 transports the substrate S from the minus side (−X-axis side) to the plus side (+X-axis side), along the X-axis as a whole. At this time, the width direction (short direction) of the belt-shape substrate S is set along the Y-axis direction.

As the substrate S which is a surface to be treated in the substrate-treating apparatus 100, for example, a resin film or a foil of stainless steel or the like can be used. For example, for the resin film, materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin can be used.

For example, the substrate S preferably has a small thermal expansion coefficient such that the size is not changed even in the case of receiving heat of about 200° C. For example, the thermal expansion coefficient can be reduced by mixing inorganic filler with a resin film. Examples of the inorganic filler include such as titanium oxide, zinc oxide, alumina, and silicon oxide. In addition, the substrate S may be a single body of ultrathin glass having a thickness of about 100 μm, prepared by a float method or the like, or a laminate formed by adhering the resin film or aluminum foil on the ultrathin glass.

The size of the width direction (short direction) of the substrate S, for example, is formed to be about 1 m to 2 m, and the size of the length direction (long direction), for example, is formed to be 10 m or more. Needless to say, the sizes are only examples and are not limited thereto. For example, the size of the Y-axis direction of the substrate S may also be 50 cm or less, or may also be 2 m or greater. In addition, the size of the X-axis direction of the substrate S may also be 10 m or less.

The substrate S is preferably formed so as to have flexibility. Here, the term flexibility refers to properties capable of flexing the substrate without being broken or fractured even in the case where a force of about its own weight is added to the substrate. In addition, properties of bending by a force of about its own weight are also included in the flexibility.

In addition, the flexibility varies depending on such as the material, the size, the thickness of the substrate, the environment such as temperature, or the like. Further, as the substrate S, a single belt-shape substrate may be used, or the substrate S may be configured to be formed in a belt-shape by connecting a plurality of unit substrates.

The substrate-supplying unit 2, for example, supplies the substrate S wound in a roll shape by sending the substrate S to the substrate-treating unit 3. In this case, in the substrate-supplying unit 2, a rotation driving device or the like that rotates a shaft portion winding the substrate S or the shaft portion is provided. In addition, the substrate-supplying unit 2 may have a configuration in which a cover portion that covers the substrate S in the state of being wound in a roll shape or the like is provided. Moreover, the substrate-supplying unit 2 is not limited to the mechanism for sending the substrate S wound in a roll shape, and may include a mechanism (for example, a nip-type driving roller) for sequentially sending the belt-shape substrate S in the length direction.

The substrate-retrieving unit 4 retrieves the substrate S that has passed through the substrate-treating apparatus 100, for example, by winding in a roll shape. In the substrate-retrieving unit 4, in the same manner as in the substrate-supplying unit 2, a rotation driving source that rotates a shaft portion for winding the substrate S or the shaft portion, a cover portion that covers the retrieved substrate S, or the like is provided. Moreover, in the case where the substrate S is cut into a panel shape or the like in the substrate-treating unit 3, for example, the substrate-treating unit 3 may have a configuration in which the substrate S is retrieved in a different state from the state of being wound in a roll shape, as a configuration in which the substrate S is retrieved in a stacked state.

The substrate-treating unit 3 transports the substrate S supplied from the substrate-supplying unit 2 to the substrate-retrieving unit 4, and performs a step of chemically modifying the surface Sa to be treated of the substrate S in a process of transporting using a fluorine-containing compound, a step of irradiating a chemically modified surface to be treated with light having a predetermined pattern, and a step of disposing a patterning material. The substrate-treating unit 3 has the fluorine-containing compound-applying unit 6 that applies a fluorine-containing compound to the surface Sa to be treated of the substrate S, the exposing unit 7 that irradiates with light, the mask 8, the patterning material-applying unit 9, and a transporting device 20 that includes a driving roller R or the like to send the substrate S under the conditions corresponding to the form of the processing treatment.

Examples of the fluorine-containing compound-applying unit 6 or the patterning material material-applying unit 9 include liquid droplet application devices (for example, a liquid droplet discharge type application device, an ink jet type application device, a spin coating type application device, a roll coating type application device, and a slot coating type application device).

Each of these devices is suitably provided along the transport path of the substrate S, and is configured to be able to produce a flexible display panel or the like by a so-called roll-to-roll method. In the present embodiment, the exposing unit 7 is provided, and devices performing the steps before and after thereof (a photosensitive layer-forming step, a photosensitive layer-developing step, or the like) are also provided in an in-line type, if desired.

Since the fluorine-containing compound of the present invention has a photodegradable group with a water-repellent group having a fluorinated alkoxy chain at the terminal, in the case where the fluorine-containing compound is attached on the substrate surface, the contact angle between the surface thereof and a liquid can be increased. In addition, a residue (amino group) having hydrophilicity can be generated by dissociating a group having a water-repellency by irradiating with light. Therefore, before and after light irradiation, the substrate surface exhibits good hydrophilicity, and the contact angle can be reduced.

The fluorine-containing compound of the present invention can be suitably used for, for example, formation of an organic thin-film layer (also referred to as a "self-organized monomolecular layer") which is used for an organic thin-film transistor.

In the self-organized monomolecular layer, the organic semiconductor material enhances wettability to improve the crystallinity (the size and the array of crystals) of the organic semiconductor material, and further, to improve the electrical connection of a source electrode and a drain electrode constituting the organic thin-film transistor with the organic semiconductor layer.

In particular, it is presumed that the applicability of the organic semiconductor material can be improved by forming a self-organized monomolecular layer using the fluorine-containing compound of the present invention on an insulating layer constituting an organic thin-film transistor and changing the wettability by exposure and also it may contribute to improving the mobility of the organic semiconductor.

EXAMPLES

Hereinafter, the present invention will be described in more detail with reference to Examples, although the present invention is not limited to the following Examples.

Examples 1

Synthesis of Fluorine-Containing Compound (1)

9.02 g (65.4 mmol) of o-dimethoxybenzene, 0.311 g (2.45 mmol) of iodine crystals, and 20.7 g (131 mmol) of isobutyric acid anhydride were put into a 100-mL recovery flask, the mixture was refluxed at 170° C. for 6 hours, returned to room temperature, and then stirred for 31 hours. Thereafter, the mixture was distilled off under reduced pressure, purified water (80 mL) was added thereto, and the organic layer was extracted with diethyl ether (80 mL×3). The organic layer was washed with a 5% aqueous sodium hydrogen carbonate solution (80 mL), saturated saline (80 mL), and purified water (80 mL), dried over anhydrous magnesium sulfate, filtered, and concentrated. The residue was isolated and purified by column chromatography (hexane:ethyl acetate=4:1), concentrated, and vacuum-dried to obtain 3.90 g (18.7 mmol, 29%) of a pale yellow viscous matter (compound (I1)).

The identification results of the above-synthesized compound (compound (I1)), 1-(3,4-dimethoxyphenyl)-2-methylpropanone, are shown below.

$^1$H-NMR (400 MHz, CDCl$_3$): δ 1.22 (6H, d, J=6.8 Hz), 3.55 (1H, sep, J=6.8 Hz), 3.94 and 3.95 (6H, s, s), 6.90 (1H, d, J=8.4 Hz), 7.55 (1H, d, J=2.0 Hz), 7.60 (1H, d, J=2.0 Hz).

IR (NaCl): 1674 (C=O) cm$^{-1}$.

[Chem. 14]

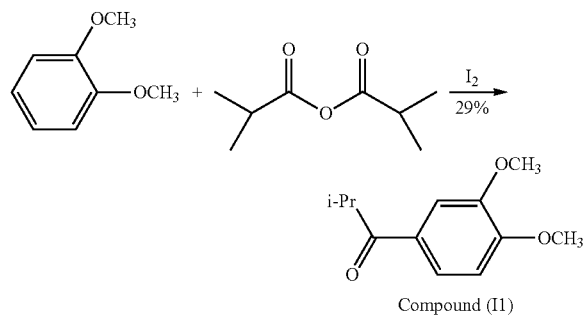

Compound (I1)

Next, 2.73 g (13.1 mmol) of the compound (I1) was put into a 100-mL two-neck recovery flask, and 50 mL of N,N-dimethylformamide (hereinafter, referred to as "DMF") as a dry solvent and 11.2 g (262 mmol: 20 eq) of lithium chloride were added thereto in a nitrogen atmosphere. The mixture was refluxed at 170° C. for 29 hours and stirred at 100° C. for 32 hours. Thereafter, 200 mL of saturated saline and 50 mL of 2 N hydrochloric acid were added thereto and the mixture was extracted with 150 mL of ethyl acetate three times. The mixture was dried over anhydrous magnesium sulfate, filtered, concentrated, and vacuum-dried. The residue was isolated and purified by column chromatography (hexane:ethyl acetate=2:1), concentrated, and vacuum-dried to obtain 1.50 g (8.30 mmol, 63%) of a yellow viscous matter (compound (I2)).

The identification results of the above-synthesized compound (compound (I2)), 1-(3,4-dihydroxyphenyl)-2-methylpropanone, are shown below.

$^1$H-NMR (400 MHz, CDCl$_3$): δ 1.21 (6H, d, J=6.8 Hz), 3.53 (1H, sep, J=6.9 Hz), 6.35 (1H, s), 6.94 (1H, d, J=8.4 Hz), 7.39 (1H, s), 7.52 (1H, d, J=8.4 Hz), 7.83 (1H, d, J=2.0 Hz).

IR (NaCl): 1656 (C=O), 3349 (OH) cm$^{-1}$.

[Chem. 15]

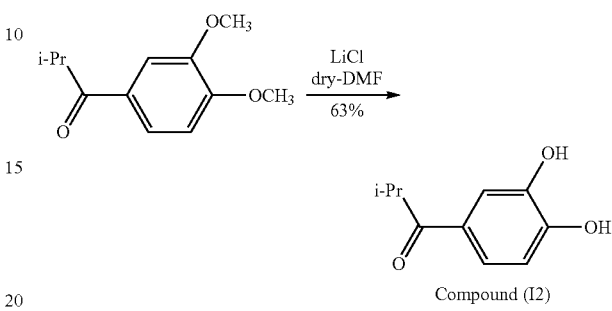

Compound (I2)

1.02 g (5.67 mmol) of the compound (I2), 15 mL of DMF, and 1.57 g (11.3 mmol: 2 eq) of potassium carbonate were put into a 100-mL two-neck recovery flask, and the mixture was stirred at room temperature for 2 hours. Thereafter, 7 mL of DMF was added to 4.64 g (12.0 mmol: 2 1 eq) of 1-iodine-1H,1H,2H,2H,3H,3H-perfluoroheptane, the mixture was added dropwise to the recovery flask, and the mixture was stirred at 60° C. for 14 hours. After the reaction solution was distilled off under reduced pressure, 60 mL of purified water and 20 mL of 2 N hydrochloric acid were added thereto, and the mixture was extracted with ethyl acetate (60 mL×4) and washed with saturated saline (60 mL×5). The organic layer was dried over anhydrous magnesium sulfate, filtered, concentrated, and vacuum-dried to obtain 3.62 g (5.17 mmol, 91%) of an orange solid (compound (I3)).

The identification results of the above-synthesized compound (compound (I3)), 1-(3,4-di(1H,1H,2H,2H,3H,3H-perfluoroheptyloxy)phenyl)-2-methylpropanone, are shown below.

$^1$H-NMR (400 MHz, CDCl$_3$): δ 1.21 (6H, d, J=6.8 Hz), 2.15-2.19 (4H, m), 2.32-2.34 (4H, m), 3.53 (1H, sep, J=6.9 Hz), 4.13 and 4.14 (4H, t, t), 6.88 (1H, d, J=8.5 Hz), 7.52 (1H, d, J=2.0 Hz), 7.58 (1H, d, J=8.4 Hz).

IR (KBr): 722 (CF$_3$), 1226 (CF$_2$, CF$_3$), 1678 (C=O) cm$^{-1}$.

[Chem. 16]

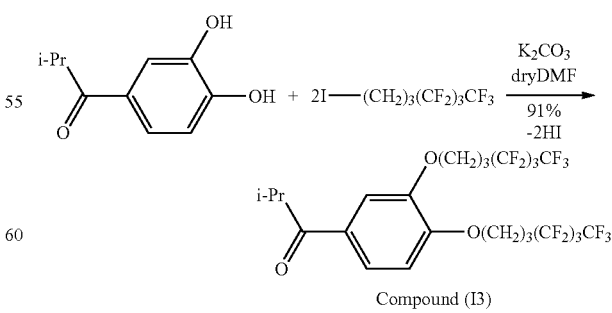

Compound (I3)

0.502 g (0.717 mmol) of the compound (I3) was put into a 100-mL recovery flask and dissolved in 3 mL of diethyl ether. 5 mL of 70% nitric acid was poured thereto in an ice bath and the mixture was stirred for 1.5 hours in an ice bath. Next, the reaction solution was poured into ice, extracted with 50 mL of purified water and ethyl acetate (50 mL×3), and washed with 5% sodium hydrogen carbonate (50 mL×3). The organic layer was dried over anhydrous magnesium sulfate, filtered, and concentrated.

The residue was recrystallized by dissolving the concentrated product in 20 mL of ethanol. The crystal was subjected to suction filtration and vacuum drying to obtain 0.256 g (3.43 mmol, 48%) of a light yellow needle-like crystal (compound (I4)).

The identification results of the above-synthesized compound (compound (I4)), 1-(2-nitro-4,5-di(1H,1H,2H,2H, 3H,3H-perfluoroheptyloxy)phenyl)-2-methylpropanone, are shown below.

$^1$H-NMR (400 MHz, CDCl$_3$): δ 1.21 (6H, d, J=6.8 Hz), 2.15-2.23 (4H, m), 2.27-2.34 (4H, m), 2.89 (1H, sep), 4.16 and 4.17 (4H, t, t), 6.67 (1H, s), 7.64 (1H, s).

IR (KBr): 721 (CF$_3$), 1228 (CF$_2$, CF$_3$), 1358 and 1523 (NO$_2$), 1703 (C=O) cm$^{-1}$.

[Chem. 17]

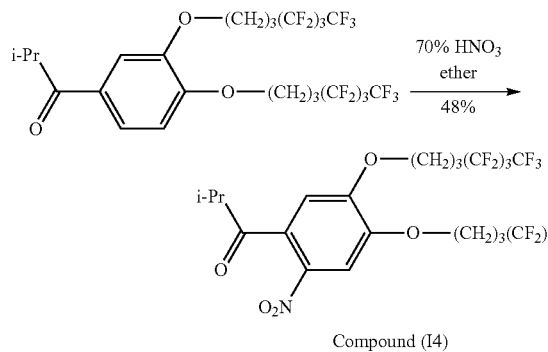

Compound (I4)

2.96 g (3.97 mmol) of the compound (I4), 12 mL of tetrahydrofuran, and 8 mL of methanol were put into a 100-mL recovery flask, 0.300 g (7.94 mmol: 2eq) of sodium borohydride was poured thereto in an ice bath, and the mixture was stirred for 90 minutes. Thereafter, the mixture was stirred at room temperature for 30 minutes. The reaction solution was concentrated and extracted with 60 mL of purified water, 20 mL of 2 N hydrochloric acid, and ethyl acetate (50 mL×3). The organic layer was dried over anhydrous magnesium sulfate, filtered, and concentrated. The residue was isolated and purified by column chromatography (hexane:ethyl acetate=6:1), concentrated, and vacuum-dried to obtain 2.17 g (2.90 mmol, 76%) of a yellow viscous matter (compound (IS)).

The identification results of the above-synthesized compound (compound (IS)), 1-(2-nitro-4,5-di(1H,1H,2H,2H, 3H,3H-perfluoroheptyloxy)phenyl)-2-methylpropan-1-ol, are shown below.

$^1$H-NMR(400 MHz, CDCl$_3$): δ 0.94 and 0.96 (6H, d, d, J=6.8 Hz), 1.97-2.03 (1H, m), 2.14-2.21 (5H, m), 2.27-2.40 (4H, m), 4.08-4.23 (4H, m), 5.27 (1H, t, J=4.8 Hz), 7.20 (1H, s), 7.55 (1H, s).

IR (NaCl): 742 (CF$_3$), 1228 (CF$_2$, CF$_3$), 1334 and 1522 (NO$_2$), 3547(OH) cm$^{-1}$.

[Chem. 18]

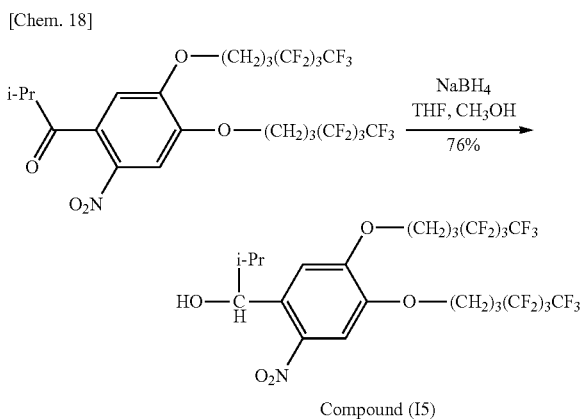

Compound (I5)

1.43 g (1.91 mmol: 1 eq.) of the (compound (IS)), 0.580 g (5.73 mmol: 3 eq.) of triethylamine, 20 mL of dry-acetonitrile, and 0.735 g (2.87 mmol: 1.5 eq.) of N-succinimidyl carbonate were put into a 100-mL two-neck recovery flask in a nitrogen atmosphere, and the mixture was stirred at room temperature for 40 hours. Thereafter, the reaction solution was concentrated, 30 mL of purified water and 5 mL of 2 N hydrochloric acid were added thereto, and the mixture was extracted with ethyl acetate (30 mL×3) and washed with 5% saline (30 mL×3). The organic layer was dried over anhydrous magnesium sulfate, filtered, and concentrated. The residue was isolated and purified by column chromatography (hexane:ethyl acetate=3:1), concentrated, and vacuum-dried to obtain 1.55 g (1.74 mmol, 91%) of a yellow viscous matter (compound (I6)).

The identification results of the above-synthesized compound (compound (I6)), 1-(2-nitro-4,5-di(1H,1H,2H,2H, 3H,3H-perfluoroheptyloxy)phenyl)-2-methylpropyl N-succinimidyl carbonate, are shown below.

$^1$H-NMR (400 MHz, CDCl$_3$): δ 1.03 and 1.11 (6H, d, d, J=7.2 Hz), 2.05-2.40 (9H, m), 2.79 (4H, s), 4.12-4.37 (4H, m), 6.38 (1H, d, J=4.8 Hz), 6.96 (1H, s), 7.65 (1H, s).

IR (NaCl): 720 (CF$_3$), 1227 (CF$_2$, CF$_3$), 1336 and 1524 (NO$_2$), 1746 (C=O) cm$^{-1}$.

[Chem. 19]

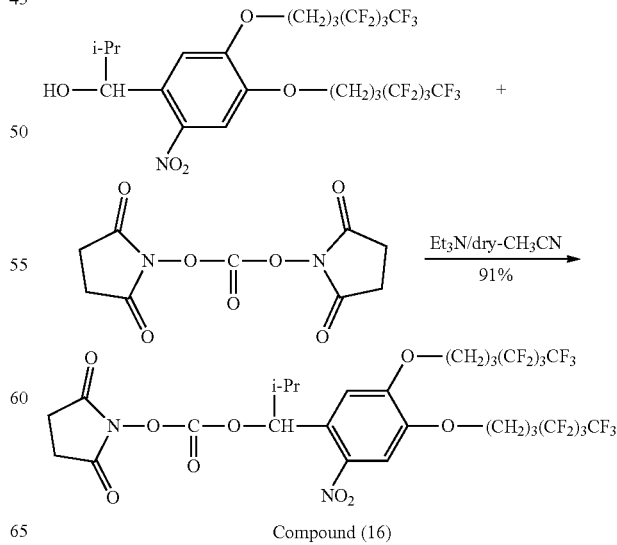

Compound (16)

0.603 g (0.680 mmol) of the (compound (I6)), 10 mL of dry-tetrahydrofuran (hereinafter referred to as "THF"), and 0.136 g (0.759 mmol: 1.1 eq) of 3-aminopropyltrimethoxysilane were put into a 30-mL two-neck recovery flask, and the mixture was stirred at room temperature for 3.5 hours. Thereafter, the reaction solution was concentrated and isolated by medium-pressure column chromatography (hexane: ethyl acetate: tetramethoxysilane=3:1:0.04), concentrated, and vacuum-dried to obtain 0.451 g (0.473 mmol, 70%) of a pale yellow solid (compound (1)).

The identification results of the above-synthesized compound (1), 1-(2-nitro-4,5-di(1H,1H,2H,2H,3H,3H-perfluoroheptyloxy)phenyl)-2-methy 1propyl N-(3-trimethoxysilyl)propylcarbamate, are shown below.

$^1$H-NMR (400 MHz, CDCl$_3$): δ 0.58-0.67 (2H, m), 0.98 (6H, dd, J=6.8, 4.0 Hz), 1.56-1.63 (2H, m), 2.10-2.20 (5H, m), 2.26-2.41 (4H, m), 3.09-3.16 (2H, m), 3.56 (9H, s), 4.10-4.15 (4H, m), 5.00 (1H, t, J=5.8 Hz), 6.20 (1H, d, J=5.2 Hz), 6.87 (1H, s), 7.57 (1H, s).

IR (KBr):720 (CF$_3$), 1227 (CF$_2$, CF$_3$), 1336 and 1524 (NO$_2$), 1746 (CO)=cm$^{-1}$.

a saturated aqueous ammonium chloride solution, and 40 mL of 1.2 N hydrochloric acid were added thereto, and the mixture was extracted with ethyl acetate (50 mL×6) and washed with a saturated aqueous sodium chloride solution (40 mL×3). The organic layer was dried over anhydrous sodium sulfate, filtered, concentrated, and vacuum-dried to obtain 3.46 g (3.97 mmol, 99%) of a white solid (compound (I21)).

The identification results of the compound obtained by the above synthesis (compound (I21)) are shown below.

$^1$H-NMR (400 MHz, CDCl$_3$): δ (ppm) 2.10-2.19 (4H, m), 2.26-2.40 (4H, m), 3.05 (3H, s), 4.12 and 4.13 (4H, t, t, J=7.2 Hz), 6.88 (1H, d, J=10.5 Hz), 7.50 (1H, d, J=2.5 Hz), 7.56 (1H, dd, J=2.5, 14.8 Hz).

$^{13}$C-NMR (100 MHz, CDCl$_3$): δ (ppm) 20.63, 26.29, 27.88, 67.35, 111.64, 112.21, 123.69, 130.91, 148.35, 152.74, 196.78.

$^{19}$F-NMR (376 MHz, CDCl$_3$): δ (ppm) −126.29 (4F), −123.53 (4F), −123.01 (4F), −122.04 (4F), −114.62 (4F), −80.92 (6F).

[Chem. 20]

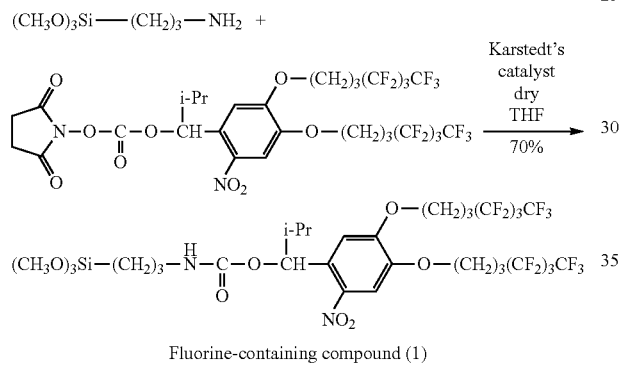

Fluorine-containing compound (1)

Example 2

Synthesis of Fluorine-Containing Compound (2)

As the Example, 1-(2-nitro-4,5-bis((4,4,5,5,6,6,7,7,8,8,9,9,9-tridecafluorononyl)oxy)phenyl)ethyl(3-(trieth oxysilyl)propyl)carbamate (fluorine-containing compound (2)) is shown. The compound was synthesized by the step shown in [Chem. 25], which will be described later.

Synthesis of 1-(3,4-Bis((4,4,5,5,6,6,7,7,8,8,8-undecafluorooctypoxy)phenypethanone (Step 1)

1-(3,4-Bis((4,4,5,5,6,6,7,7,8,8,8-undecafluorooctypoxy) phenypethanone (compound (I21)) was synthesized by the step shown below.

1.11 g (8.03 mmol) of potassium carbonate was metered into a 100-mL three-neck recovery flask, 10 mL of DMF and 0.61 g (4.01 mmol) of 1-(3,4-dihydroxyphenyl)ethanone were added thereto while purging the inside of the reactor with nitrogen, and the mixture was stirred at room temperature for 10 minutes. Thereafter, 4.00 g (8.20 mmol) of 1,1,1,2,2,3,3,4,4,5,5,6,6-tridecafluoro-9-iodonate which had been dissolved in 8 mL of DMF was added dropwise thereto and the mixture was stirred at room temperature for 24 hours. Thereafter, the mixture was warmed to 60° C. and stirred for 1 hour. The reaction solution was distilled off under reduced pressure, 20 mL of purified water, 60 mL of

[Chem. 21]

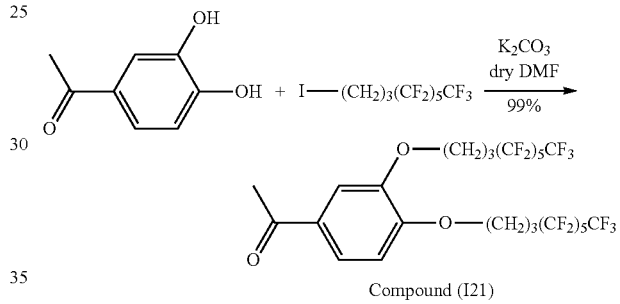

Compound (I21)

Synthesis of 1-(2-Nitro-4,5-bis((4,4,5,5,6,6,7,7,8,8,9,9,9-tridecafluorononyl)oxy)phenyl)ethanone
(Step 2)

1-(2-Nitro-4,5-bis((4,4,5,5,6,6,7,7,8,8,9,9,9-tridecafluorononyl)oxy)phenypetha none (compound (I22)) was synthesized by the step shown below.

100 g (1.15 mmol) of 1-(3,4-bis((4,4,5,5,6,6,7,7,8,8,9,9,9-tridecafluorononyl)oxy)phenypethanone was put into a 50-mL three-neck recovery flask and dissolved in 3 mL of acetic acid. Further, 3 mL of 60% nitric acid which had been dissolved in 2 ml of acetic acid was added dropwise thereto, and the mixture was warmed to 50° C. and stirred for 4 hours. Thereafter, 100 ml of ice water was added to the inside of the reactor, and the mixture was extracted with ethyl acetate (50 mL×6) and washed with a saturated aqueous sodium hydrogen carbonate solution (50 mL×3). The organic layer was dried over anhydrous sodium sulfate, filtered, and concentrated. The residue was isolated and purified by flash column chromatography (hexane:ethyl acetate=5:1 to 0:1), concentrated, and vacuum-dried to obtain 0.84 g (0.92 mmol, 80%) of an off-white solid (compound (I22)).

The identification results of the compound obtained by the above synthesis (compound (I22)) are shown below.

$^1$H-NMR (400 MHz, CDCl$_3$): δ (ppm) 2.15-2.21(4H, m), 2.27-2.39(4H, m), 2.48(3H, s), 4.16 and 4.16(4H, t), 6.64 (1H, s), 7.59(1H, s).

$^{13}$C-NMR (100 MHz, CDCl$_3$): δ (ppm) 20.46, 27.68, 30.47, 67.80, 108.15, $^{19}$F-NMR (376 MHz, CDCl$_3$): δ (ppm)-126.28(4F), -123.52(4F), -123.01(4F), -122.03(4F), -114.64(4F), -80.84(6F).

[Chem. 22]

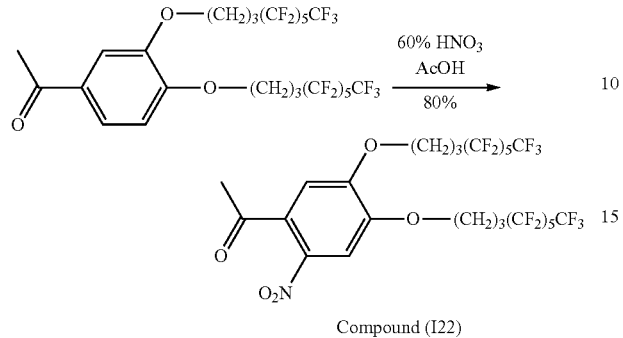

Compound (I22)

Synthesis of 1-(2-Nitro-4,5-bis((4,4,5,5,6,6,7,7,8,8,9,9,9-tridecafluorononyl)oxy)phenyl)ethanol (Step 3)

1-(2-Nitro-4,5-bis((4,4,5,5,6,6,7,7,8,8,9,9,9-tridecafluorononyl)oxy)phenypethanol (compound (I23)) was synthesized by the step shown below.

0.080 g (2.11 mmol) of sodium borohydride, 1 mL of tetrahydrofuran, and 1 mL of methanol were put into a 50-mL recovery flask, and the mixture was stirred for 5 minutes. 2 mL of tetrahydrofuran, and 0.84 g (0.92 mmol) of 1-(2-nitro-4,5-bis((4,4,5,5,6,6,7,7,8,8,9,9,9-tridecafluorononyl)oxy)phenyl)ethanone which had been dissolved in 2 mL of methanol were put into another container and added dropwise slowly at 0° C. After 15 minutes, the mixture was warmed to room temperature and stirred for 45 minutes. The reaction solution was concentrated and extracted with 5 mL of purified water, 20 ml of a saturated aqueous ammonium chloride solution, and ethyl acetate (50 mL×4). The organic layer was dried over anhydrous sodium sulfate, filtered, and concentrated. The residue was isolated and purified by flash column chromatography (hexane:ethyl acetate=10:1 to 3:1), concentrated, and vacuum-dried to obtain 0.40 g (0.43 mmol, 80%) of a yellowish green viscous matter (compound (I23)).

The identification results of the compound obtained by the above synthesis (compound (I23)) are shown below.

$^1$H-NMR (400 MHz, CDCl$_3$): δ (ppm) 2.12-2.20 (4H, m), 2.27-2.40 (5H, m), 4.10-4.20 (3H, m), 7.29 (1H, s), 7.55 (1H, s).

$^{13}$C-NMR (100 MHz, CDCl$_3$): δ (ppm) 20.05, 24.45, 27.76, 65.81, 67.59, 109.34, 109.84, 137.25, 139.84, 146.96, 153.17.

$^{19}$F-NMR (376 MHz, CDCl$_3$): δ (ppm)-126.27 (4F), -123.52 (4F), -123.00 (4F), -122.02 (4F), -114.62 (4F), -80.86 (6F).

[Chem. 23]

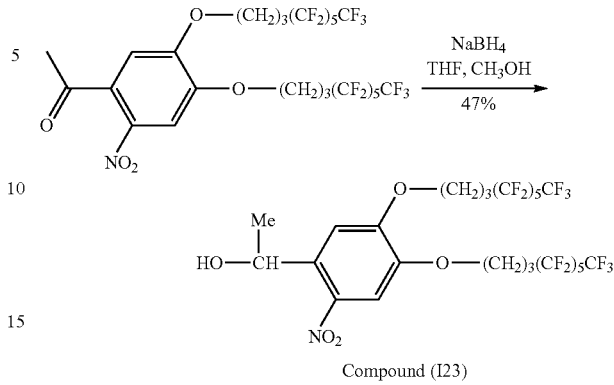

Compound (I23)

Synthesis of 1-(2-Nitro-4,5-bis((4,4,5,5,6,6,7,7,8,8,9,9,9-tridecafluorononyl)oxy)phenyl)ethyl(3-(triet hoxysilyl)propyl)carbamate (Step 4)

1-(2-Nitro-4,5-bis((4,4,5,5,6,6,7,7,8,8,9,9,9-tridecafluorononyl)oxy)phenyl)ethyl (3-(triethoxysilyl)propyl)carbamate(fluorine-containing compound (2)) was synthesized by the step shown below.

0.24 g (0.26 mmol) of 1-(2-nitro-4,5-bis((4,4,5,5,6,6,7,7,8,8,9,9,9-tridecafluorononyl)oxy)phenyl)ethanol, 3 mL of tetrahydrofuran, and 0.17 g (0.71 mmol) of triethoxy(3-isocyanatopropyl)silane were added to a 30-mL recovery flask under nitrogen, and dibutyl tin dilaurate which had been dissolved in 2 mL of tetrahydrofuran was added dropwise thereto. After stirring at room temperature for 30 minutes, the mixture was heated and refluxed, and stirred for 21 hours. The reaction solution was concentrated, isolated by flash silica gel column chromatography (hexane:ethyl acetate=10:1 to 3:1), concentrated, and vacuum-dried to obtain 0.29 g (0.25 mmol, 93%) of a pale yellow solid (fluorine-containing compound (2)).

The identification results of the compound obtained by the above synthesis (fluorine-containing compound (2)) are shown below.

$^1$H-NMR (400 MHz, CDCl$_3$): δ (ppm) 0.56-0.64 (4H, m), 1.18-1.24 (12H, m), 1.55-1.65 (5H, m), 2.11-2.19 (4H, m), 2.24-2.40 (4H, m), 3.05-3.50 (2H, m), 3.77-3.83 (6H, m), 4.08-4.16 (4H, m), 5.03 (1H, t), 6.33 (1H, q), 6.97 (1H, s), 7.56 (1H, s).

$^{13}$C-NMR (100 MHz, CDCl$_3$): δ (ppm) 7.67, 18.13, 20.49, 22.14, 23.20, 27.72, 43.34, 58.42, 67.53, 67.65, 68.55, 109.45, 109.54, 134.63, 140.06, 147.10, 152.95, 155.23.

$^{19}$F-NMR (376 MHz, CDCl$_3$): δ (ppm)–126.27 (4F), –123.54 (4F), –123.01 (4F), –122.03 (4F), –114.64 (4F), –80.88 (6F).

[Chem. 24]

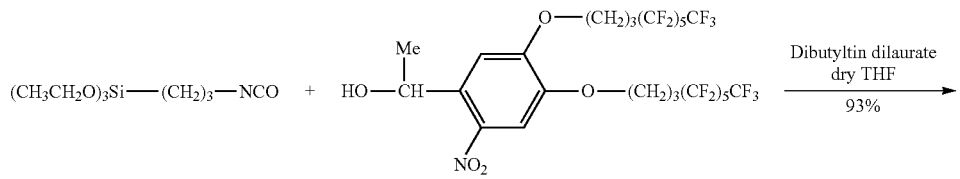

-continued

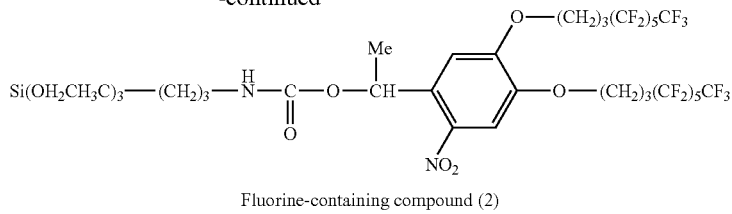

Fluorine-containing compound (2)

The synthesis route of 1-(2-nitro-4,5-bis((4,4,5,5,6,6,7,7,8,8,9,9,9-tridecafluoro phenyl)oxy)phenyl)ethyl(3-(triethoxysilyl)propyl)carbamate (fluorine-containing compound (2)) is shown below.

[Chem. 25]

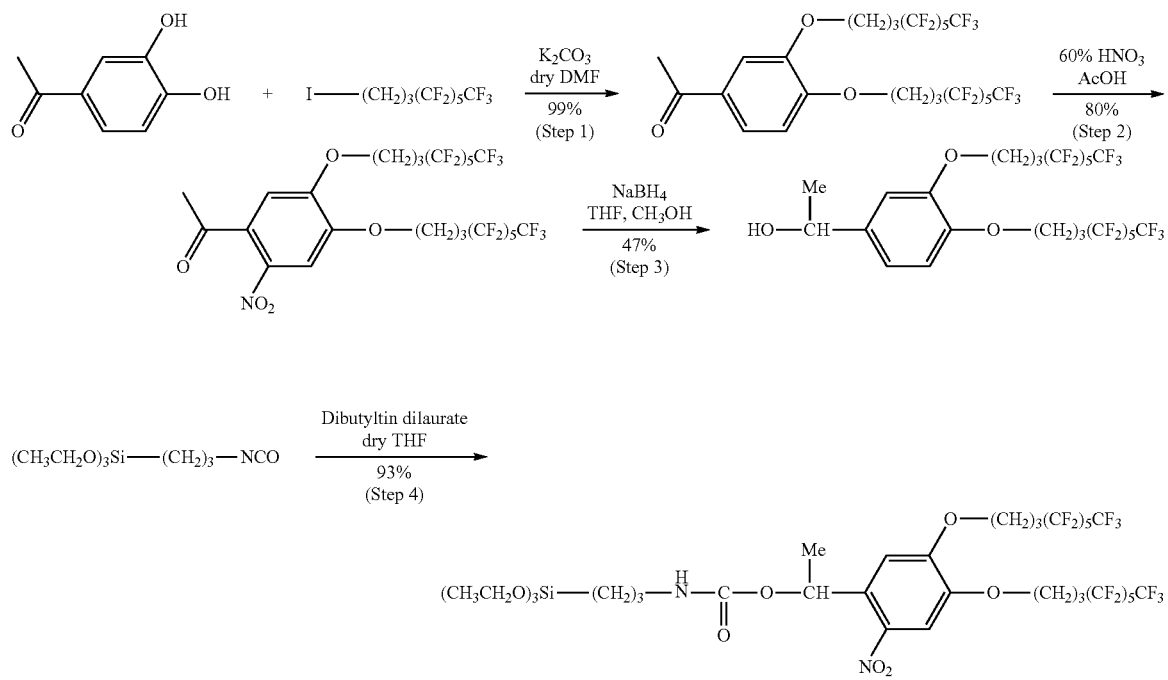

Example 3

Surface Modification of Substrate with Fluorine-Containing Compound (1)

The substrate was subjected to surface modification using the fluorine-containing compound (1) obtained by the above synthesis method.

With respect to the modified substrate obtained, the static contact angle of water was measured and the surface density was calculated using UV. The photodegradation was tracked by a change in the static contact angle of water, and a comparison between before and after light irradiation by X-ray photoelectron spectroscopy (hereinafter referred to as "XPS") and X-ray reflectometer (hereinafter referred to as "XRR") was carried out.

[Pretreatment Step]

A silicon wafer (3.5 cm×1.5 cm) and quartz glass (4 cm×1 cm) were subjected to a pretreatment with a UV-ozone cleaner.

A silicon wafer and quartz glass were subjected to ultrasonic washing for 5 minutes with methanol, pure water, and acetone, respectively. Then, the substrate was taken out and dried in a stream of nitrogen, the mirror surface of the silicon wafer was irradiated with UV for 1.5 hours, and both sides of the quartz glass was pretreated for 1.5 hours, using a UV-ozone cleaner. The oxygen injection into the UV-ozone cleaner was performed at a flow rate of 6 L/min for 3 minutes and UV irradiation was performed for 1.5 hours. The generated ozone was discharged by flowing nitrogen at a flow rate of 6 L/min for 10 minutes.

[Surface Modification Step]

Subsequently, 20 mL of a dry toluene solution and 19.1 mg (20.0 µmol) of the fluorine-containing compound (1) were put into a 50-mL recovery flask, thereby preparing a 1 mM solution in the recovery flask. The substrate which had been subjected to the pretreatment was put into this recovery flask, heated at 100° C., and immersed for 1 hour. The substrate was washed with methanol and subjected to ultrasonic washing with methanol and chloroform, respectively, for 10 minutes, and dried in a stream of nitrogen. This substrate was used in Example 3.

In Comparative Example 1, the substrate was modified by the same method as above except that the following compound (11) was used as a modifying compound.

[Chem. 26]

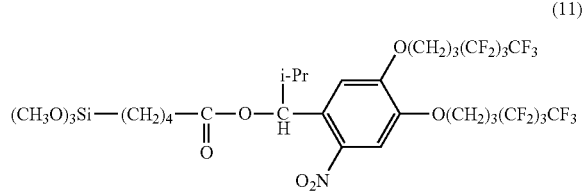

(11)

In Example 3, it is presumed that the chemical modification of the substrate was carried out as follows.

[Chem. 27]

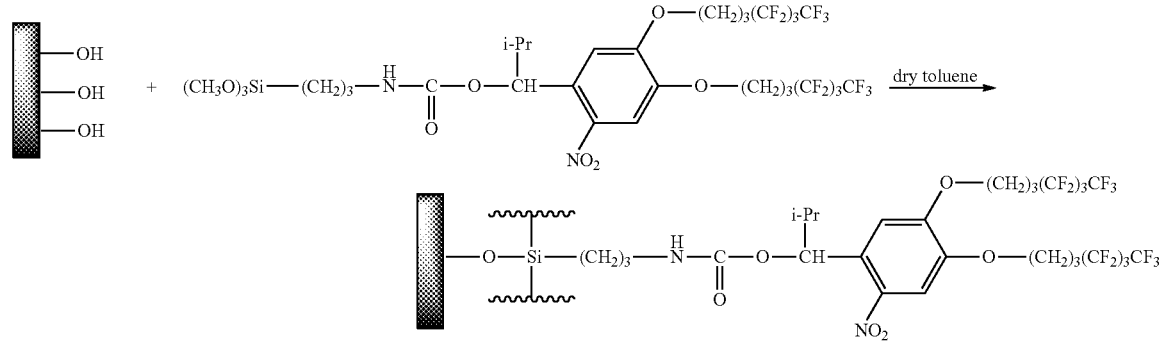

In Example 3, it is presumed that the substrate was modified from the viewpoints that the static contact angle of water of the obtained substrate surface was 101° for the silicon wafer and 100° for the quartz glass, both of which exhibited hydrophobicity. Further, from the results of the XPS measurement, it was demonstrated that modifications could be carried out from the viewpoint that F peaks appeared on the substrate after the modification. The results are shown in Table 1. In addition, the surface density calculated from UV in the quartz glass was $1.7 \times 10^{14}$ molecules/cm$^2$.

<<Light Irradiation onto Modified Substrate>>

Thereafter, in order to investigate the photodegradation of the modified substrate thus obtained, light irradiation at an intensity of 25 mW/cm$^2$ was carried out through a copper sulfate filter that shields light at a wavelength of 320 nm or less, by an ultrahigh-pressure mercury lamp. The substrate after the light irradiation was washed with methanol and chloroform, subjected to ultrasonic washing for 5 minutes with chloroform, and dried in a stream of nitrogen.

The photodegradation was performed as in the following scheme, and when the light was irradiated, a nitroso compound was dissociated by the photodegradation of a

[Chem. 28]

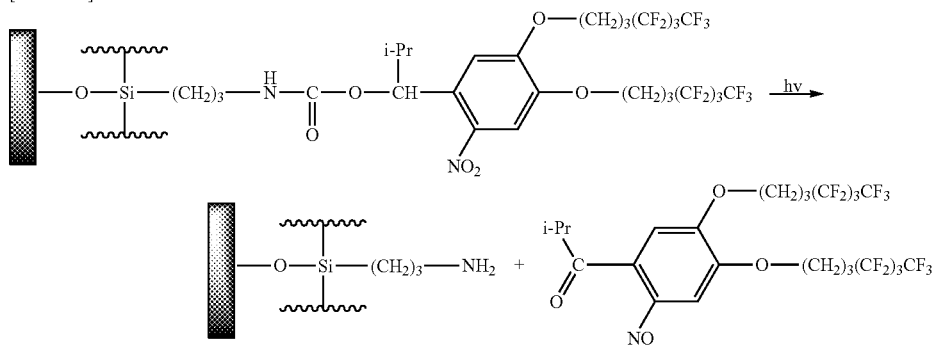

nitrobenzyl group, whereby an amino group can be introduced into the substrate surface.

Figure 2:
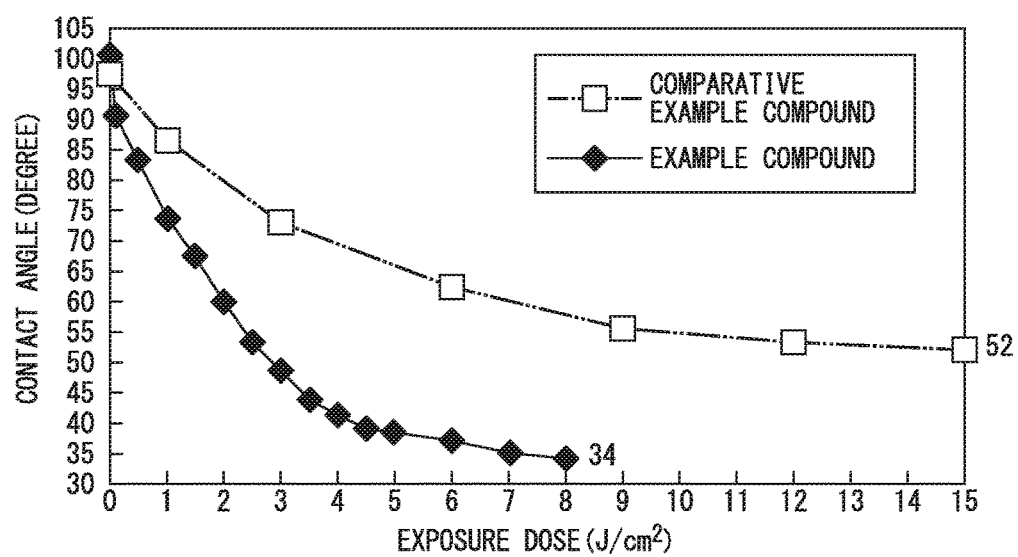
FIG. 2 is a view showing the measured results of a change in static contact angles of water with lapse of time in Examples of the present invention.

FIG. 2 shows the results of the measurement of a change in the static contact angles of water over time by irradiating the substrates of Example 3 and Comparative Example 1 (both substrates are silicon wafer substrates) with light. In FIG. 2, the Comparative Example compound represents Comparative Example 1 and Example compound represents Example 3.

From the change in the static contact angles of water by irradiating the modified substrate shown in FIG. 2 with light, in Example 3, from the viewpoint that the contact angle decreased according to the exposure dose and finally, the surface became hydrophilic at 34°, it was confirmed that the photodegradation proceeded. In addition, it could be also confirmed that dissociation of the photodegradable group occurred from the viewpoint that F decreased to a larger extent than that of the compositional ratio of the respective elements shown in Table 1.

In addition, the difference in the contact angles between before and after the light irradiation in Example 3 was larger than that in Comparative Example 1.

The compositional ratios of the respective elements when the elemental compositional ratio of Si—Si determined from the XPS spectrum before and after the substrates of Example 3 and Comparative Example 1 (both substrates are silicon wafer substrates) were irradiated with light was normalized as 1 are shown in Table 1 below.

TABLE 1

| | $C_{1s}$ | | $N_{1s}$ $(NO_2)$ | | $F_{1s}$ | | Si—Si | |
|---|---|---|---|---|---|---|---|---|
| | After modifi-cation | After exposure | After modifi-cation | After exposure | After modifi-cation | After exposure | After modifi-cation | After exposure |
| Example 3 | 0.81 | 0.69 | 0.053 | 0.0043 | 0.7 | 0.013 | 1 | 1 |
| Comparative Example 1 | 0.58 | 0.44 | 0.016 | 0.0087 | 0.54 | 0.043 | 1 | 1 |

As shown in Table 1, it could be confirmed that the peaks of the element based on the photodegradable group are lost and the photodegradable group is dissociated by exposure.

<<Experimental Examples of Surface Modification in 2-Steps>>

As shown in the following Experimental Example 1, Experimental Examples in which the substrate surface is subjected to a 2-step surface modification using the fluorine-containing compound of the present invention are described.

First, the contact angle could be changed from 101° to 34° by subjecting the silicon wafer substrate to surface modification using the fluorine-containing compound of the present invention and performing exposure ($\lambda > 320$ nm, 25 mW/cm$^2$), (see (A) and (B) in [First Step] of the following Experimental Example 1).

Next, the compound (C) was allowed to undergo a reaction with the (B) obtained in the first step in 80 μL of triethylamine and 20 mL of dry DMSO at room temperature for 40 hours. Thus, it could be confirmed that the 2-step surface modification can be performed since the contact angle of the substrate surface was changed to 75° (see (D) in [Second Step] of the following Experimental Example 1).

[Chem. 29]

[First step]

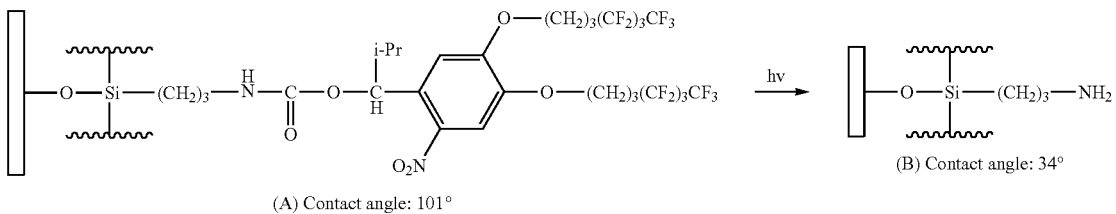

(A) Contact angle: 101°

(B) Contact angle: 34°

[Second step]

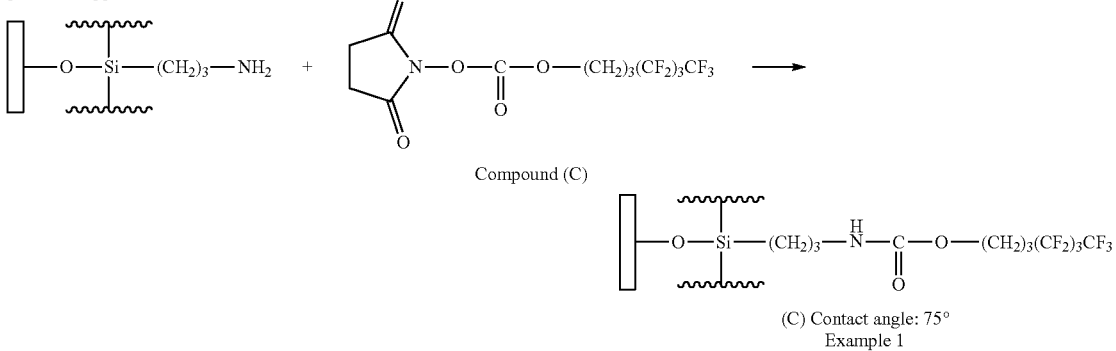

Compound (C)

(C) Contact angle: 75°
Example 1

The XPS measurement results and the XRR measurement results of (A), (B), and (D) in Experimental Example with the 2-step surface modification are shown in Tables 2 and 3, respectively.

TABLE 2

|   | $C_{1S}$ | $N_{1S}$ | $F_{1S}$ | Si—Si |
|---|---|---|---|---|
| (A) | 0.81 | 0.053 | 0.7 | 1 |
| (B) | 0.69 | 0.043 | 0.013 | 1 |
| (D) | 0.63 | 0.045 | 0.37 | 1 |

TABLE 3

| | Thickness (nm) Found value/Calculated value |
|---|---|
| (A) | 1.9/2.1 |
| (B) | 0.99/0.6 |
| (D) | 1.3/1.3 |

As shown from the above results, it could be confirmed that a surface modification can be performed in 2-steps also from the XPS measurement results and the XRR measurement results. Thus, it may be possible that hydrophilic-water-repellent patterns and the adhesion with an organic semiconductor can also be satisfied.

REFERENCE SIGNS LIST

S: Substrate
CONT: Controlling unit
Sa: Surface to be treated
2: Substrate-supplying unit
3: Substrate-treating unit
4: Substrate-retrieving unit
6: Fluorine-containing compound-applying unit
7: Exposing unit
8: Mask
9: Pattern forming materialmaterial-applying unit
100: Substrate-treating apparatus

What is claimed is:

1. A method for producing a fluorine-containing compound represented by the following General formula (1):

(1)

$X_3Si(CH_2)_n$—NH—C(=O)—O—CH(R$^1$)—[aryl with R$^{f1}$, R$^{f2}$, O$_2$N substituents]

wherein
X represents a halogen atom or an alkoxy group,
R$^1$ represents a hydrogen atom or a linear, branched, or cyclic alkyl group having 1 to 10 carbon atoms,
R$^{f1}$ and R$^{f2}$ are each independently a fluorinated alkoxy group, and
n represents an integer of 0 or more,
the method comprising:
performing a first reaction represented by following formula 1:

(formula 1)

R$^1$—C(=O)—[phenyl-3,4-(OH)$_2$] + I—R$^{f1'}$ + I—R$^{f2'}$ ⟶

R$^1$—C(=O)—[phenyl-3-R$^{f1}$-4-R$^{f2}$];

after the first reaction, performing a second reaction represented by following formula 1-1:

(formula 1-1)

R$^1$—C(=O)—[phenyl-3-R$^{f1}$-4-R$^{f2}$] $\xrightarrow{HNO_3}$ R$^1$—C(=O)—[phenyl-3-R$^{f1}$-4-R$^{f2}$-5-NO$_2$];

after the second reaction, performing a third reaction represented by following formula 1-2:

(formula 1-2)

R$^1$—C(=O)—[phenyl-R$^{f1}$, R$^{f2}$, O$_2$N] $\xrightarrow{CH_3OH}$ HO—CH(R$^1$)—[phenyl-R$^{f1}$, R$^{f2}$, O$_2$N];

after the third reaction, performing a fourth reaction represented by following formula 1-3:

(formula 1-3)

HO—CH(R$^1$)—[phenyl-R$^{f1}$, R$^{f2}$, O$_2$N] + [N-hydroxysuccinimide carbonate, (NHS)$_2$CO] ⟶

-continued

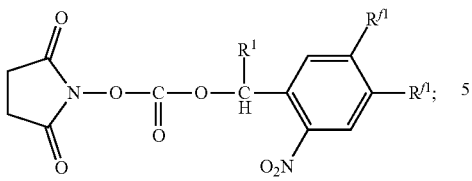

after the fourth reaction, performing a fifth reaction represented by following formula 2:

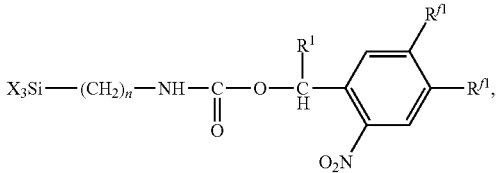

wherein
$R^{f1'}$ and $R^{f2'}$ are each independently a fluorinated alkyl group,
X represents a halogen atom or an alkoxy group,
$R^1$ represents a hydrogen atom or a linear, branched, or cyclic alkyl group having 1 to 10 carbon atoms,
$R^{f1}$ and $R^{f2}$ are each independently a fluorinated alkoxy group, and
n represents an integer of 0 or more.

2. The method for producing a fluorine-containing compound according to claim 1, wherein the fluorine-containing compound is a photodegradable coupling agent.

3. The method of producing the fluorine-containing compound according to claim 1, wherein the fifth reaction represented by the formula 2 is conducted with dry-tetrahydrofuran (dry-THF).

* * * * *

UNITED STATES PATENT AND TRADEMARK OFFICE
CERTIFICATE OF CORRECTION

PATENT NO. : 11,518,731 B2  
APPLICATION NO. : 16/193526  
DATED : December 6, 2022  
INVENTOR(S) : Kazuo Yamaguchi et al.

Page 1 of 1

It is certified that error appears in the above-identified patent and that said Letters Patent is hereby corrected as shown below:

On the Title Page

(73) Assignee:  
Replace "NIKON CORPORATION, Tokyo (JP)"  
With -- KANAGAWA UNIVERSITY, Yokohama (JP);  
NIKON CORPORATION, Tokyo (JP) --.

Signed and Sealed this  
Twenty-seventh Day of December, 2022

Katherine Kelly Vidal  
*Director of the United States Patent and Trademark Office*